United States Patent
Aung et al.

[11] Patent Number: 5,243,990
[45] Date of Patent: Sep. 14, 1993

[54] BLOOD PRESSURE MONITOR SYSTEM

[75] Inventors: Ye Aung, Komaki; Hideo Nishibayashi, Inuyama; Masayuki Shinoda, Tajimi, all of Japan

[73] Assignee: Colin Electronics Co., Ltd., Aichi, Japan

[21] Appl. No.: 828,688

[22] Filed: Jan. 31, 1992

[30] Foreign Application Priority Data

Feb. 16, 1991 [JP] Japan .................. 3-044203

[51] Int. Cl.$^5$ .................................... A61B 5/02
[52] U.S. Cl. ................... 128/677; 128/680; 128/681
[58] Field of Search ................ 128/677-684, 128/6

[56] References Cited

U.S. PATENT DOCUMENTS

4,479,494 10/1984 McEwen ................ 128/682

Primary Examiner—Lee S. Cohen
Assistant Examiner—Robert L. Nasser, Jr.
Attorney, Agent, or Firm—Oliff & Berridge

[57] ABSTRACT

A blood pressure measure system for iteratively measuring a blood pressure of a living subject at predetermined intervals of time, the monitor system including a pressing device pressing a body portion of the subject; a regulating device regulating the pressing force of the pressing device; a blood pressure measuring device iteratively measuring at least a systolic blood pressure of the subject at the intervals of time, each of the iterative blood pressure measurements being effected when the pressing force of the pressing device is decreased at a predetermined rate by the regulating device; a pulse rate measuring device measuring, as a pulse rate, a pulse number per unit time of the subject; a first determining device determining, by utilizing the pulse rate, a pressing force increase amount such that as the pulse rate is increased the increase amount is decreased; and a second determining device determining a target pressing force to be greater by the increase amount than a systolic blood pressure measured in a preceding blood pressure measuring cycle, the blood pressure measuring device effecting a current blood pressure measurement when the pressing force of the pressing device is decreased at the predetermined rate after being increased to the target pressing force.

11 Claims, 3 Drawing Sheets

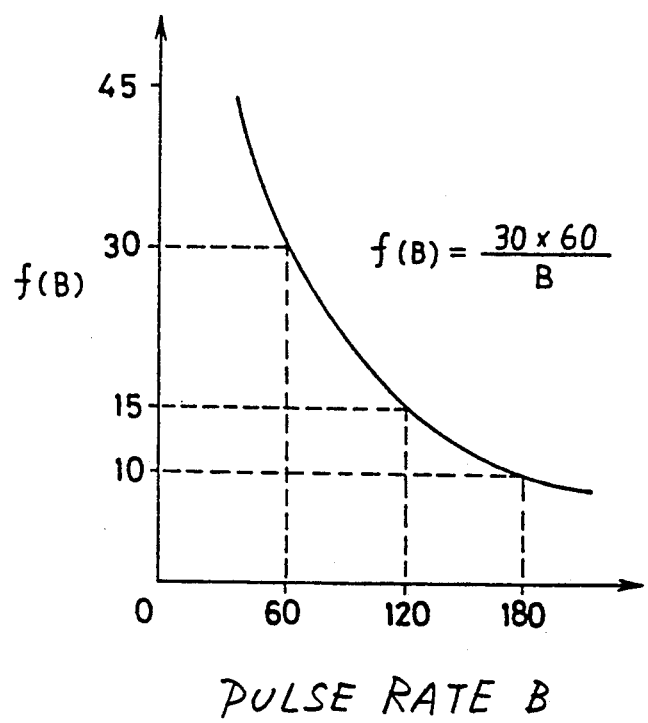

BLOOD PRESSURE MONITOR SYSTEM

BACKGROUND OF THE INVENTION

1. Field of the Invention

The present invention relates in general to a blood pressure monitor device, and more particularly to such a device which iteratively measures a blood pressure of a subject during a pressing force decreasing operation.

2. Related Art Statement

There is known a blood pressure monitor system including a pressing device such as an inflatable cuff for pressing a body portion of a subject; and a measuring device which increases the pressing force of the pressing device, subsequently decreases the pressing force, and measures a blood pressure of the subject based on Korotkoff sounds or pulse wave obtained during decreasing of the pressing force, the measuring device repeating the blood pressure measurement at predetermined regular intervals of time. In the conventional monitor system, the measuring device increases the pressing force to a target pressure which is a predetermined high level (e.g., 180 mmHg), and subsequently reduces the pressing force at a low rate (e.g., 2 to 3 mmHg/sec). However, the measuring device is incapable of measuring a systolic blood pressure of the subject which is higher than the target pressure. In this case, the measuring device is required to increase the pressing force to a level higher by a suitable amount than the systolic blood pressure. To prevent this problem, another known monitor system is adapted to increase the pressing force to a target pressure which is higher by a predetermined amount than a systolic blood pressure obtained in a preceding blood pressure measuring cycle.

However, in the above described second monitor system, the target pressure is constantly set at the level higher by a predetermined pressure than the previously obtained systolic blood pressure, without considering variety of subjects. Therefore, for some subjects, the target pressure may be unnecessarily high. Consequently, those subjects may feel uneasiness or pain, and the time necessary for the pressing force increasing operation may be unnecessarily long, which leads to increasing the time necessary for the blood pressure measurement. More specifically, in the blood pressure monitoring system of the Korotkoff-sound type, a Korotkoff sound is detected when the pressing force which has been increased to the target pressure is reduced to the level of systolic blood pressure. However, the detected sound may not be the first Korotkoff sound, but a noise signal. For judging whether or not the detected sound is the true, first Korotkoff sound, the system is required to continue reading in the signal for a predetermined length of time corresponding to, for example, at least three sounds. On the other hand, the monitor system of the oscillometric type determines, as a systolic pressure, a pressing force (e.g., cuff pressure) at the time of the first inflection point of the amplitudes of pulses detected during the pressure reducing operation. However, for identifying the first inflection point, the system is required to continue reading in the signal for a predetermined length of time corresponding to, for example, at least five pulses which include the inflection point as a middle data point or pulse. Therefore, the reading time necessary for reading in the signal or data for detecting the first Korotkoff sound or the first inflection point varies depending upon pulse rates of subjects. Namely, the reading time for a subject whose pulse rate is fast is short, while the time for a subject whose pulse rate is slow is long. For this reason, in the conventional monitor systems, the predetermined amount to be added to the prior systolic blood pressure is required to be a sufficiently large value (e.g. 50 mmHg) so as to provide a reading time long enough for the subject whose pulse rate is slow. On the other hand, for the patient whose pulse rate is fast, the target pressure thus determined becomes unnecessarily high, whereby the patient may feel uneasiness or pain and the time necessary for the blood pressure measurement is unnecessarily increased.

SUMMARY OF THE INVENTION

It is therefore an object of the present invention to provide a blood pressure monitor system wherein the target pressing force is set at a level higher than a systolic blood pressure determined in the preceding measuring cycle by an amount which is a minimum increase amount corresponding to the pulse number of a subject, thereby reducing the burden to the subject caused by the pressing force and reducing the time necessary for the blood pressure measuring operation.

The above object has been achieved by the present invention, which provides a blood pressure monitor system for iteratively measuring a blood pressure of a living subject at predetermined intervals of time, the monitor system comprising (a) pressing means for pressing a body portion of the subject, (b) regulating means for regulating the pressing force of the pressing means, (c) blood pressure measuring means for iteratively measuring at least a systolic blood pressure of the subject at the intervals of time, each of the iterative blood pressure measurements being effected when the pressing force of the pressing means is decreased at a predetermined rate by the regulating means, (d) pulse rate measuring means, as a pulse rate, a pulse number per unit time of the subject, (e) first determining means for determining, by utilizing the pulse rate, a pressing force increase amount such that as the pulse rate is increased the increase amount is decreased, and (f) second determining means for determining a target pressing force to be greater by the increase amount than a systolic blood pressure measured in a preceding blood pressure measuring cycle, the blood pressure measuring means effecting a current blood pressure measurement when the pressing force of the pressing means is decreased at the predetermined rate after being increased to the target pressing force.

In the blood pressure monitor system constructed as described above, the pulse rate measuring means measures as a pulse rate a pulse number per unit time of a subject, and the first determining means determines, based on the pulse rate, a pressing force increase amount such that, as the pulse rate is increased, the increase amount is decreased. Thus, the increase amount and the target pressing force are determined to be minimum corresponding to the pulse rate of the subject. That is, the present system prevents the increase amount from being unnecessarily large for a subject whose pulse rate is high, thereby reducing the burden to the subject caused by the pressing force and reducing the time necessary for increasing the pressing force and the overall time for the blood pressure measurement.

According to a preferred feature of the present invention, the pressing means comprises an inflatable cuff, and means for supplying the cuff with pressurized fluid.

According to another feature of the present invention, the regulating means comprises means for detecting the fluid pressure in the cuff, and means for deflating the cuff from a target pressure corresponding to the target pressing force.

According to yet another feature of the present invention, the blood pressure measuring means comprises means for detecting a pressure pulse wave transmitted to the cuff from the body portion of the subject when the cuff is deflated by the regulating means, and means for determining as the systolic blood pressure a fluid pressure in the cuff at a time of detection of an inflection point of amplitudes of respective pulses of the pulse wave.

According to a further feature of the present invention, the regulating means decreases the pressing force of the pressing means at a predetermined amount per unit time. Alternatively, the regulating means may decrease the pressing force of the pressing means at a predetermined amount per arterial pulse.

In a preferred embodiment of the present invention, the pulse rate measuring means measures a time between successive two arterial pulses of the subject and determines the pulse rate by dividing 60 seconds by the time.

In another embodiment of the present invention, the first determining means determines the pressing force increase amount, ΔP, by the following equation (1):

$$\Delta P = \alpha + f(B) \quad (1)$$

where $\alpha$ is a constant value, and $f(B)$ is a function of the pulse rate, the function $f(B)$ being decreased as the pulse rate is increased.

In the above embodiment of the invention, the second determining means may determine the target pressing force, $P_m$, by the following equation (2):

$$P_m = SYS1 + \Delta P \; (= \alpha + f(B)) \quad (2)$$

where SYS1 is the systolic blood pressure measured in the preceding blood pressure measuring cycle.

In yet another embodiment of the present invention, the regulating means increases the pressing force of the pressing means to a predetermined high level as a target pressing force for an initial blood pressure measuring cycle.

In a further embodiment of the present invention, the system further comprises means for displaying at least the systolic blood pressure measured by the blood pressure measuring means.

BRIEF DESCRIPTION OF THE DRAWINGS

The above and optional objects, features and advantages of the present invention will be better understood by reading the following detailed description of the presently preferred embodiment of the invention when considered in conjunction with the accompanying drawings, in which:

FIG. 3 is a graph of a function, f(B), included in the increase amount $\Delta P (= \alpha + f(B))$ determined in the flow chart of FIG. 2.

DERAILED DESCRIPTION OF THE PREFERRED EMBODIMENT

Figure 1:
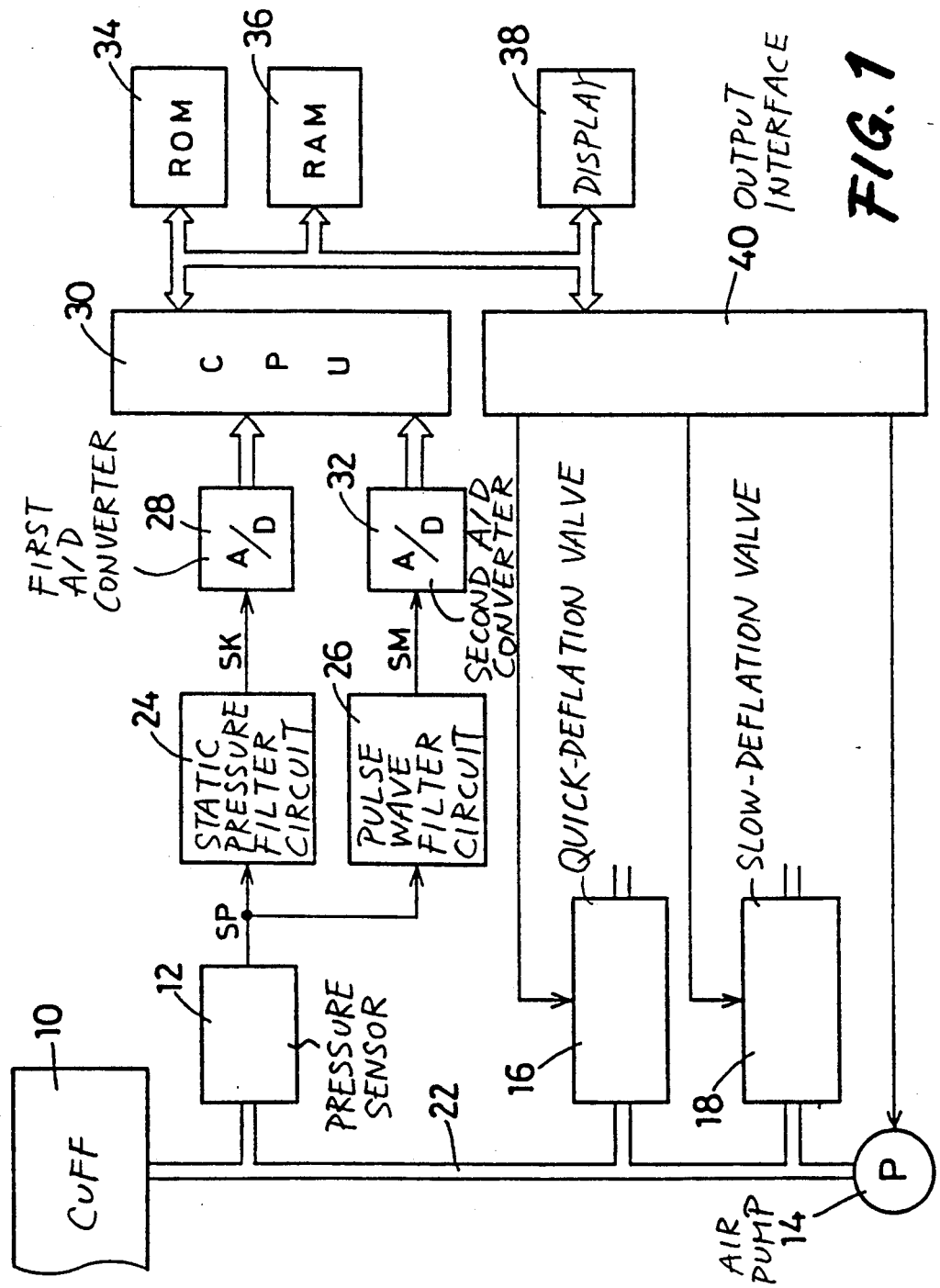
FIG. 1 is a diagrammatic view of a blood pressure monitor system embodying the present invention.

Referring first to FIG. 1, there is shown a blood pressure monitor system embodying the present invention.

In FIG. 1, reference numeral 10 denotes a rubber cuff which is adapted to be set around an upper arm or the like of a living subject. A pressure sensor 12, an air pump 14, a quick-deflation valve 16 and a slow-deflation valve 18 are connected to the cuff 10 via piping 22, respectively. In the present embodiment, the cuff 10 serves as pressing means. The pressure sensor 12 detects the air pressure in the cuff 10 (hereinafter, referred to as the "cuff pressure"), and produces pressure signal SP representing the detected cuff pressure, to a static pressure filter circuit 24 and a pulse wave filter circuit 26. The static pressure filter circuit 24 includes a low-pass filter which, upon supply of the pressure signal SP, transmits only a cuff pressure signal SK representing a static pressure of the cuff pressure, to a central processing unit (CPU) 30 via a first analog to digital (A/D) converter 28. Meanwhile, the pulse wave filter circuit 26 includes a band-pass filter which transmits only a pulse wave signal SM out of the pressure signal SP, to the CPU via a second A/D converter 32. The pulse wave signal SM represents oscillatory pressure wave transmitted to the cuff 10 in synchronism with heartbeat of the subject. In the present embodiment, the pressure sensor 12, air pump 14, quick-deflation valve 16 and slow-deflation valve 18 serve as regulating means for regulating the pressing force of the pressing means.

The CPU 30 is connected via data bus to a read only memory (ROM) 34, a random access memory (RAM) 36, a display 38, and an output interface 40. The CPU 30 processes input signals by utilizing the control programs pre-stored in the ROM 34 and the temporary-storage function of the RAM 36, and regulates via respective drive circuits (not shown) the air pump 14, quick- and slow-deflation valves 16, 18. In addition, the CPU 30 operates for determining at least a systolic blood pressure of the subject by utilizing the pulse wave signal SM and the cuff pressure signal SK which are obtained during decreasing of the cuff pressure, and commands the display 38 to indicate the determined blood pressure. The CPU 30 iteratively effects the blood pressure measurement at predetermined regular intervals of time, and the display 38 indicates the last measured, i.e., current blood pressure.

Figure 2:
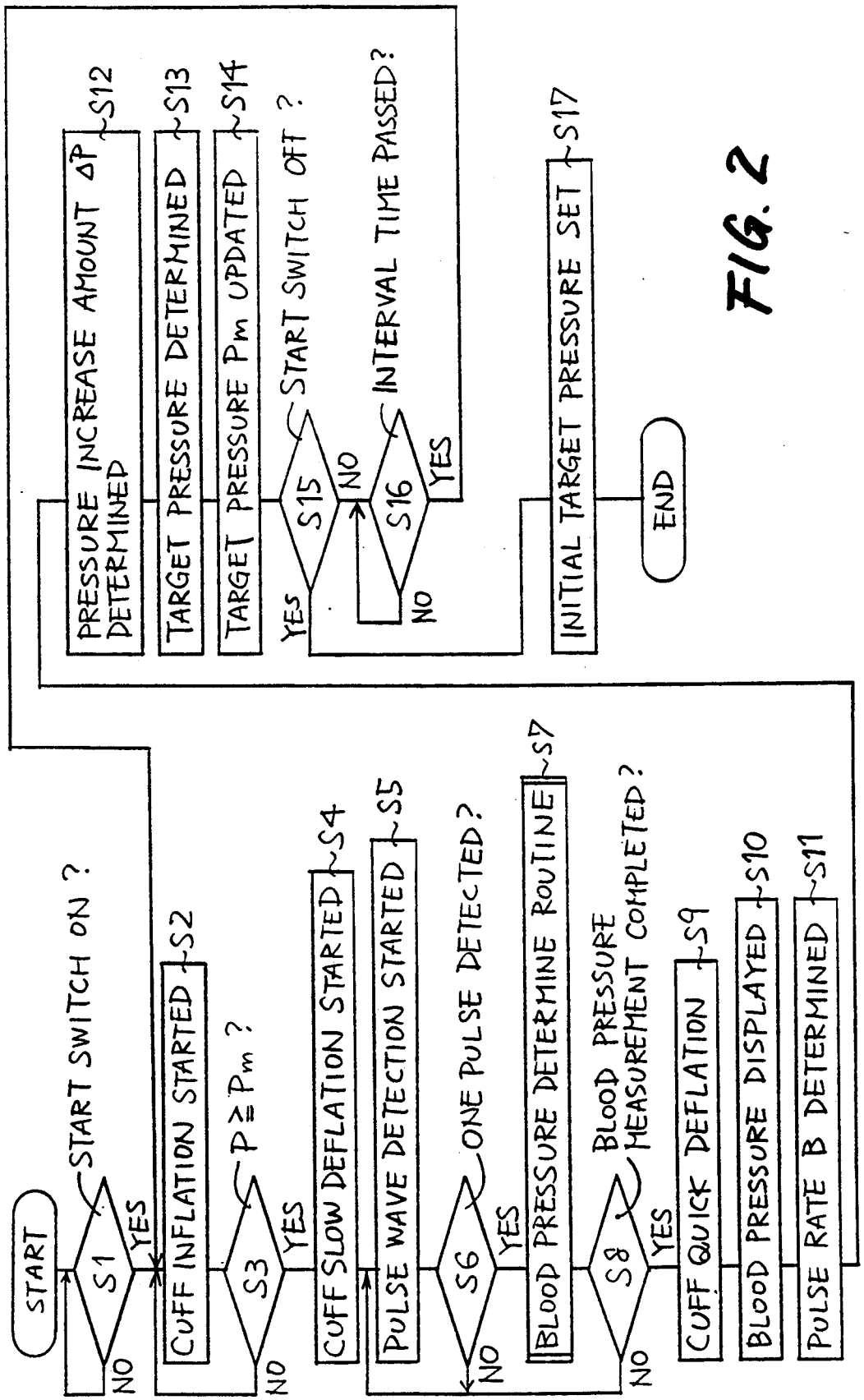
FIG. 2 is a flow chart for illustrating the operation of the monitor system of FIG. 1.

Hereinafter, there will be described the operation of the blood pressure monitor system constructed as described above, by reference to the flow chart of FIG. 2.

Upon application of electric power to the monitor system, the CPU 30 effects initialization operations (not shown), and subsequently the control of the CPU 30 proceeds with Step S1 to identify whether or not a start switch (not shown) has been turned ON. If a negative decision is obtained in Step S1, the control of the CPU 30 repeats Step S1 until an affirmative decision is obtained. On the other hand, if an affirmative decision is obtained in Step S1, the control goes to Step S2. In Step S2, both the quick- and slow-deflation valves 16, 18 are closed and the air pump 14 is driven or rotated by the drive circuit therefor, so that the cuff pressure starts to be increased. Subsequently, the control of the CPU 30 goes to Step S3 to identify whether or not the cuff pressure, P, has exceeded a target cuff pressure $P_m$. The present monitor system is adapted such that the target cuff pressure $P_m$ is initially set at a predetermined, high pressure level (e.g., 180 mmHg). If the cuff pressure P has not exceeded the target cuff pressure $P_m$ and therefore a negative decision is obtained in Step S3, the control repeats Steps S2 and S3 until an affirmative decision is obtained. On the other hand, if an affirmative decision is made in Step S3, the control goes to Step S4 in which the rotation of the air pump 14 is stopped and the slow-deflation valve 18 is opened. Consequently, the cuff pressure P starts to be decreased at a predetermined low rate. This pressure decrease rate may be either a pressure decrease per time or a pressure decrease per pulse (i.e., arterial pulse).

Step S4 is followed by Step S5 in which the CPU 30 starts reading in the pulse wave signal SM. Step S5 is followed by Step S6 to identify whether or not the CPU 30 has read in one pulse of the signal SM corresponding to one-time heart beat of the subject. If a negative decision is made in Step S6, the CPU 30 repeats Steps S5 and S6 until an affirmative decision is obtained. If an affirmative decision is made in Step S6, the control goes to Step S7 to implement the blood pressure determining routine. In the blood pressure determining routine of Step S7, a well known algorithm is used for effecting the oscillometric blood pressure determining method. In this method, a systolic and a diastolic blood pressure are determined as respective cuff pressures P at the time of detection of specific two pulses of the pulse wave. Specifically, the CPU 30 first determines, as a mean blood pressure, a cuff pressure P at the time of detection of a pulse having the greatest amplitude of the amplitudes of the respective pulses read in during decreasing of the cuff pressure. In addition, the CPU 30 determines, as a systolic blood pressure, a cuff pressure P at the time of an inflection point of the amplitudes which point is located on a higher-pressure side of the mean blood pressure, and as a diastolic blood pressure a cuff pressure P at the time of an inflection point of the amplitudes which point is located on a lower-pressure side of the mean blood pressure. For identifying each of the inflection points, are needed, for example, five pulses which include as a time-wise middle data point the pulse corresponding to the each inflection point. Subsequently, Step S8 is implemented to judge whether or not the blood pressure measurement has been completed. If a negative decision is made in Step S8, the control repeats Steps S5 through S8 until an affirmative decision is made. If an affirmative decision is made in Step S8, the control of the CPU 30 goes to Step S9 in which the quick-deflation valve 16 is opened. Thus, the cuff pressure P in the cuff 10 is quickly reduced, and in the subsequent Step S10 the CPU 30 commands the display 38 to indicate the determined blood pressure values. In the present embodiment, Steps S5 through S8 serve as blood pressure measuring means.

Subsequently, step S11 is implemented to measure a pulse number per unit time, B, of the subject. The pulse number per unit time B is obtained by determining an average time between successive two pulses detected or read in during the cuff pressure decreasing operation and dividing sixty seconds by the determined average time (i.e., one pulse or beat time). Step S11 is followed by Step S12 in which a pressure increase amount ΔP to be utilized in the subsequent blood pressure measuring cycle is determined according to the following expression (1). Subsequently, in Step S13, a target cuff pressure $P_m$ to be used in the subsequent measuring cycle is determined according to the expression (2). In the present embodiment, Step S11 serves as pulse rate measuring means, Step S12 serves as determining means for determining a pressing force increase amount, and Step S13 serves as determining means for determining a target pressing force, respectively.

$$\Delta P = \alpha + f(B) \quad (1)$$

$$P_m = SYS1 + \Delta P \ (= \alpha + f(B)) \quad (2)$$

In the expressions (1) and (2), symbol SYS1 denotes the systolic blood pressure measured in the present blood pressure measuring cycle, and symbol ΔP denotes an increase amount to be added to the systolic blood pressure SYS1. The increase amount ΔP includes a predetermined amount, α, which enables the present system to effect the subsequent blood pressure measurement even if the subsequent systolic blood pressure may be higher than the present systolic blood pressure SYS1 by the amount α (e.g. 20 mmHg); and an amount, f(B), which is a function of the above described pulse number per unit time B. The increase amount (function) f(B) corresponds to the pulse number per unit time B, and therefore represents the reading time necessary for reading in the least number of data points or pulses for determining the systolic blood pressure. The increase amount f(B) is pre-determined to have a relationship with the decrease rate of the cuff pressure P, such that the increase amount f(B) is decreased as the pulse number per unit time B is increased. Therefore, as the pulse number B is increased, the total increase amount ΔP is decreased, and thus the target cuff pressure $P_m$ is also decreased. An example of the function (increase amount) f(B) is shown in FIG. 3. In the figure, f(B) is defined by $30 \times 60/B$ (f(B)=$30 \times 60/B$). Therefore, in the case where the pulse number B is 60, then the increase amount f(B) is 30 mmHg and the total increase amount ΔP is 50 mmHg; in the case where the pulse number B is 120, the increase amount f(B) is 15 mmHg and the total increase amount ΔP is 35 mmHg; and in the case where the pulse number B is 180, the increase amount f(B) is 10 mmHg and the total increase amount ΔP is 30 mmHg.

Subsequently, step S14 is implemented in which the target cuff pressure $P_m$ used in Step S3 of the present blood measuring cycle is updated to the target cuff pressure $P_m$ determined in Step S13. Step S14 is followed by Step S15 to judge whether or not the start switch is turned OFF. If a negative decision is obtained, the control goes to Step S16 to judge whether or not a predetermined interval time (e.g., 5 to 10 minutes) has elapsed. If a negative decision is obtained in Step S16, the CPU 30 waits for an affirmative decision. On the otherhand, if an affirmative decision is obtained in Step S16, the control goes back to step S2 and commences the subsequent blood pressure measuring cycle. In Step S3 of this (subsequent) cycle, the cuff pressure P is increased to the target cuff pressure $P_m$ determined in the preceding measuring cycle and corresponding to the pulse number B of the subject. In this manner, the blood pressure measurements are iteratively effected at the predetermined intervals of time, and the blood pressure values are updated on the display 38. When the start switch is turned OFF and an affirmative decision is made in Step S15, the control goes to Step S17 to reset the current target cuff pressure $P_m$ to the predetermined initial value. Thus, the operation of the present monitor system is terminated.

In the present embodiment, the pulse number per unit time B is measured at each blood pressure measuring cycle, and the increase amount $\Delta P(=\alpha+f(B))$ for the subsequent measuring cycle is determined based on the measured pulse number per unit time B. The amount $\alpha$ as the first term of the increase amount $\Delta P$ is a predetermined, constant value, and the amount $f(B)$ as the second term of the amount $\Delta P$ is pre-determined such that the increase amount $f(B)$ is reduced as the pulse number B is increased. This leads to reducing the total increase amount $\Delta P$, and therefore the target cuff pressure $P_m$ for the subsequent measuring cycle which pressure is equal to the sum of the increase amount $\Delta P$ and the present systolic blood pressure SYS1. That is, the subsequent target cuff pressure $P_m$ is set at a minimum value depending upon the pulse number B of the subject, namely, minimum value which is higher than the pressure (SYS1+$\alpha$) by the amount $f(B)$ which corresponds to the pulse number B of the subject. Accordingly, in the subsequent measuring cycle, a systolic blood pressure higher by the increase amount $\alpha$ than the blood pressure SYS1 can be measured. In addition, in the case where the pulse rate of the subject is high, the discomfort of the subject caused by the pressing force applied by the cuff 10 is reduced since the time necessary for effecting the blood pressure measurement is reduced.

Further, in the present embodiment, the pulse number B is measured based on the pulse wave obtained during the pressure reducing operation, according to software program pre-stored in the ROM 34. Thus, the present monitor system is not required to accommodate an exclusive hard ware pulse rate measuring means.

Although, in the illustrated embodiment, the pressure increase amount $\Delta P$ is obtained as the value, $\alpha+f(B)$, where the $f(B)$ is decreased as the pulse number B is increased, it is possible to determine the increase amount $\Delta P$ as a value, $\alpha-f(B)'$, wherein the increase amount $\alpha$ is a constant value (e.g. 50 mmHg) and the amount $f(B)'$ is increased as the pulse number B is increased. In this case, too, the increase amount P is decreased as the pulse number B is increased. The functions $f(B)$ and $f(B)'$ may be linear functions.

Furthermore, although in the illustrated embodiment a pulse number B is measured after a current blood pressure measuring cycle is completed and subsequently an increase amount $\Delta P$ and a target cuff pressure $P_m$ for the subsequent measuring cycle are determined, it is possible to determine an increase amount $\Delta P$ and a target cuff pressure $P_m$ for a current measuring cycle, based on a pulse number B obtained in the preceding measuring cycle, before starting of the pressure increasing operation for the current blood pressure measuring cycle. In addition, the monitor system may be adapted such that a pulse number B is determined during the pressure increasing operation for a current blood pressure measuring cycle and an increase amount $\Delta P$ and a target cuff pressure $P_m$ are determined based on the determined pulse number B. In the latter case, although the pulse number B may be measured based on the pulse wave obtained during increasing of the cuff pressure, it is possible to determine a pulse number B by giving a pause to the pressure increasing operation at a predetermined pressure level and detecting pulse wave while the operation is at the pause.

Although, in the illustrated embodiment, the pulse number B is determined based on the pulse wave detected through the inflatable cuff 10, the pulse number B may be determined based on a signal generated by a pulse wave sensor pressed on a radial artery via skin, or by an electrocardiogram.

The illustrated embodiment relates to a blood pressure monitor system of the oscillometric type. However, the present invention may be applied to a blood pressure monitor system of the Korotkoff-sound type. In the Korotkoff-sound type monitor system, too, an increase amount (referred to as the function $f(B)$ in the illustrated embodiment) corresponding to the reading time necessary for detecting initial Korotkoff sounds (at lease three sounds), and a total increase amount (referred to as the value $\Delta P$ in the illustrated embodiment) are determined based on a pulse number per unit time of a subject. Thus, the Korotkoff-sound type monitor system enjoys the same advantages as those of the illustrated, oscillometric type monitor system.

It is to be understood that the present invention may be embodied with various other changes, improvements and modifications that may occur to those skilled in the art without departing from the scope and the spirit of the invention defined in the appended claims.

What is claimed is:

1. A blood pressure measure system for iteratively measuring a blood pressure of a living subject at predetermined intervals of time, the monitor system comprising:

pressing means for pressing a body portion of said subject;

regulating means for regulating the pressing force of said pressing means;

blood pressure measuring means for iteratively measuring at least a systolic blood pressure of said subject at said intervals of time, each of said iterative blood pressure measurements being effected while the pressing force of said pressing means is decreased at a predetermined rate by said regulating means;

pulse rate measuring means for measuring, as a pulse rate, a pulse number per unit time of said subject;

first determining means for determining, by utilizing said pulse rate, a pressing force increase amount such that as said pulse rate is increased said increase amount is decreased; and second determining means for determining a target pressing force to be greater by said increase amount than a systolic blood pressure measured in a preceding blood pressure measuring cycle, said blood pressure measuring means effecting a current blood pressure measurement while the pressing force of said pressing means is decreased at said predetermined rate after being increased to said target pressing force.

2. The system as set forth in claim 1, wherein said pressing means comprises:

an inflatable cuff; and means for supplying said cuff with pressurized fluid.

3. The system as set forth in claim 2, wherein said regulating means comprises:

means for detecting the fluid pressure in said cuff; and means for deflating said cuff from a target pressure corresponding to said target pressing force.

4. The system as set forth in claim 3, wherein said blood pressure measuring means comprises:

means for detecting a pressure pulse wave transmitted to said cuff from said body portion of said subject when said cuff is deflated by said regulating means; and means for determining as said systolic blood pressure a fluid pressure in said cuff at a time of detection of an inflection point of amplitudes of respective pulses of said pulse wave.

5. The system as set forth in claim 1, wherein said regulating means decreases the pressing force of said pressing means at a predetermined amount per unit time.

6. The system as set forth in claim 1, wherein said regulating means decreases the pressing force of said pressing means at a predetermined amount per arterial pulse.

7. The system as set forth in claim 1, wherein said pulse rate measuring means measures a time between successive two arterial pulses of said subject and determines said pulse rate by dividing 60 seconds by said time.

8. The system as set forth in claim 1, wherein said first determining means determines said pressing force increase amount, $\Delta P$, by the following equation (1):

$$\Delta P = \alpha + f(B) \tag{1}$$

where $\alpha$ is a constant value, and $f(B)$ is a function of said pulse rate, said function $f(B)$ being decreased as said pulse rate is increased.

9. The system as set forth in claim 8, wherein said second determining means determines said target pressing force, $P_m$, by the following equation (2):

$$P_m = SYS1 + \Delta P \ (= \alpha + f(B)) \tag{2}$$

where SYS1 is said systolic blood pressure measured in said preceding blood pressure measuring cycle.

10. The system as set forth in claim 1, wherein said regulating means increases the pressing force of said pressing means to a predetermined high level as a target pressing force for an initial blood pressure measuring cycle.

11. The system as set forth in claim 1, further comprising means for displaying at least said systolic blood pressure measured by said blood pressure measuring means.

* * * * *